(12) United States Patent
Balczewski et al.

(10) Patent No.: US 11,678,847 B2
(45) Date of Patent: Jun. 20, 2023

(54) POWER NOISE REDUCTION FOR AN INTEGRATED BATTERY

(71) Applicant: Cardiac Pacemakers, Inc., St. Paul, MN (US)

(72) Inventors: Ron A. Balczewski, Bloomington, MN (US); William J. Linder, Golden Valley, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 1173 days.

(21) Appl. No.: 15/787,977

(22) Filed: Oct. 19, 2017

(65) Prior Publication Data

US 2018/0103908 A1    Apr. 19, 2018

Related U.S. Application Data

(60) Provisional application No. 62/410,365, filed on Oct. 19, 2016.

(51) Int. Cl.
*A61B 5/00*    (2006.01)
*A61B 5/24*    (2021.01)
(Continued)

(52) U.S. Cl.
CPC .......... *A61B 5/7217* (2013.01); *A61B 5/0022* (2013.01); *A61B 5/0031* (2013.01); (Continued)

(58) Field of Classification Search
CPC ... A61B 5/7217; A61B 5/0022; A61B 5/0031; A61B 5/0422; A61B 5/686; A61B 5/0205; A61B 5/04017; A61B 5/042; A61B 5/0809; A61B 5/1112; A61B 5/1116; A61B 5/1118; A61B 5/14542; A61B 5/4866; A61B 2560/0214; A61B 2560/0468; A61B 2562/0204; A61B 2562/0209;
(Continued)

(56) References Cited

U.S. PATENT DOCUMENTS 5,314,451 A * 5/1994 Mulier .................. H01M 50/20
607/33
9,220,911 B2   12/2015 Gordon et al.
(Continued)

OTHER PUBLICATIONS

International Search Report and Written Opinion issued in PCT/US2017/057307, dated Mar. 19, 2018, 12 pages.

*Primary Examiner* — Adam Z Minchella
(74) *Attorney, Agent, or Firm* — Faegre Drinker Biddle & Reath LLP

(57) ABSTRACT

A medical device includes a case and a core assembly. The core assembly includes operational circuitry enclosed within a core assembly housing. The medical device also includes a battery assembly, which includes a battery enclosed within a battery housing. The case includes the core assembly housing and the battery housing. A first electrode is coupled to, and electrically isolated from, the case; and a second electrode is electrically coupled to the case. The second electrode is electrically coupled to the operational circuitry via a sensing pathway that includes a portion of the case. The battery is electrically coupled to the operational circuitry via an energy supply pathway that includes the portion of the case.

18 Claims, 7 Drawing Sheets

(51) Int. Cl.
- *G16H 40/67* (2018.01)
- *A61B 5/287* (2021.01)
- *A61N 1/05* (2006.01)
- *A61N 1/375* (2006.01)
- *A61N 1/378* (2006.01)
- *H01M 10/42* (2006.01)
- *A61B 5/11* (2006.01)
- *A61N 1/39* (2006.01)
- *A61B 5/145* (2006.01)
- *A61B 5/0205* (2006.01)
- *A61B 5/283* (2021.01)
- *A61B 5/316* (2021.01)
- *A61B 5/08* (2006.01)

(52) U.S. Cl.
CPC ............. *A61B 5/287* (2021.01); *A61B 5/686* (2013.01); *A61N 1/0504* (2013.01); *A61N 1/378* (2013.01); *A61N 1/3754* (2013.01); *G16H 40/67* (2018.01); *H01M 10/4257* (2013.01); A61B 5/0205 (2013.01); A61B 5/0809 (2013.01); A61B 5/1112 (2013.01); A61B 5/1116 (2013.01); A61B 5/1118 (2013.01); A61B 5/14542 (2013.01); A61B 5/283 (2021.01); A61B 5/316 (2021.01); A61B 5/4866 (2013.01); A61B 2560/0214 (2013.01); A61B 2560/0468 (2013.01); A61B 2562/0204 (2013.01); A61B 2562/0209 (2013.01); A61B 2562/0219 (2013.01); A61B 2562/166 (2013.01); *A61N 1/3956* (2013.01); *A61N 1/3975* (2013.01); *H01M 2010/4271* (2013.01)

(58) Field of Classification Search
CPC ...... A61B 2562/0219; A61B 2562/166; G16H 40/67; A61N 1/0504; A61N 1/3754; A61N 1/378; A61N 1/3956; A61N 1/3975; H01M 2/0202; H01M 10/4257; H01M 2010/4271

See application file for complete search history.

(56) References Cited

U.S. PATENT DOCUMENTS

| | | | | |
|---|---|---|---|---|
| 2003/0040779 | A1* | 2/2003 | Engmark | A61N 1/3754 607/36 |
| 2008/0275531 | A1* | 11/2008 | Bulkes | A61B 5/301 607/62 |
| 2011/0190842 | A1* | 8/2011 | Johnson | H01M 10/425 600/561 |
| 2011/0247204 | A1* | 10/2011 | Viavattine | H01M 10/0431 29/730 |
| 2013/0345770 | A1* | 12/2013 | Dianaty | A61B 5/283 607/36 |
| 2013/0345777 | A1* | 12/2013 | Feldman | A61N 1/3925 607/62 |
| 2015/0073507 | A1* | 3/2015 | Reinke | A61N 1/378 607/61 |

* cited by examiner

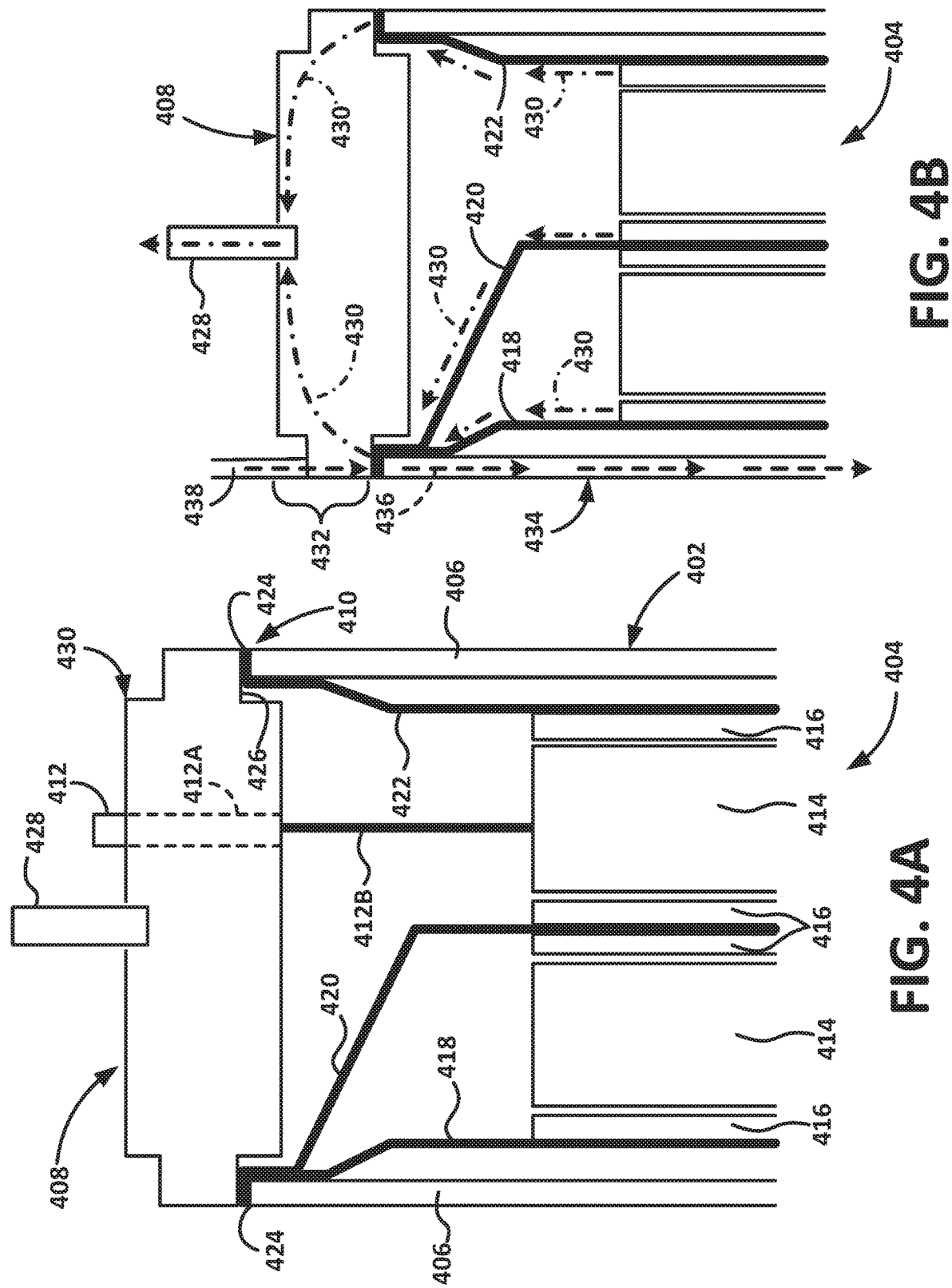

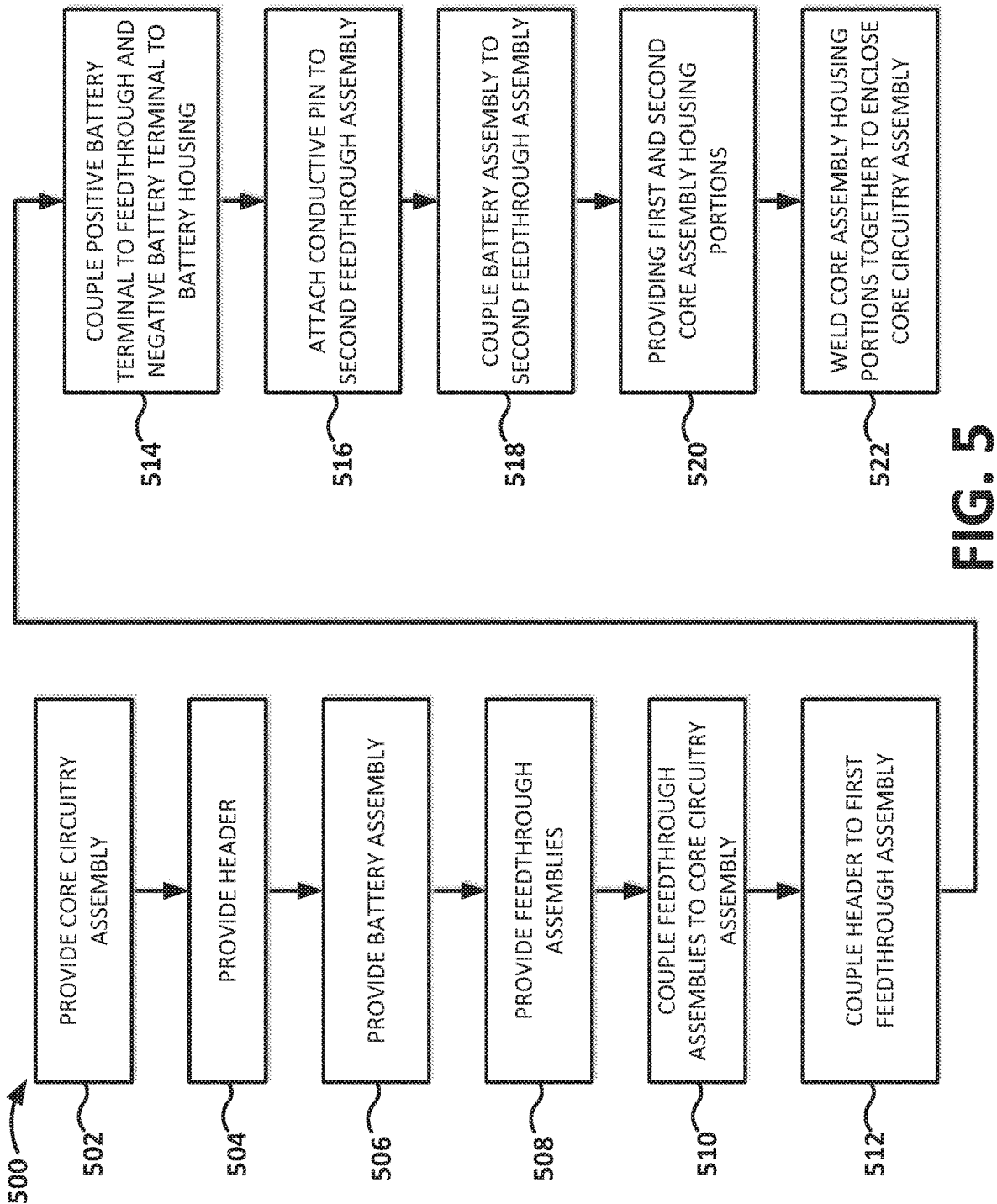

POWER NOISE REDUCTION FOR AN INTEGRATED BATTERY

CROSS-REFERENCE TO RELATED APPLICATION

This application claims priority to Provisional Application No. 62/410,365, filed Oct. 19, 2016, which is herein incorporated by reference in its entirety.

TECHNICAL FIELD

Embodiments of the present disclosure relate to medical devices and systems for sensing physiological parameters. More specifically, embodiments of the disclosure relate to battery connection configurations of implantable medical devices.

BACKGROUND

Implantable medical devices (IMDs) may be configured to sense physiological parameters and/or provide therapy and may include one or more electrodes for performing aspects of these functions (e.g., sensing electrodes). The overall usable volume enclosed within a housing of an IMD may be adjusted based on considerations of patient comfort and performance. Examples of IMDs include implantable cardiac monitors (ICMs), implantable loop recorders (ILRs), and the like, which can be configured to be subcutaneously implanted in a patient for monitoring one or more physiological parameters such as, e.g., physiological parameters associated with the heart and/or the lungs.

To facilitate a more comfortable and efficient experience, these devices, which often are powered by an internal battery, may be designed to keep the overall volume of the device as small as possible. One way of reducing volume is to use the battery housing as part of the overall device case, as opposed to disposing the battery assembly (including the battery housing) within a device case. To further increase the efficient use of space in this type of device, one of the sensing electrodes may be electrically coupled to the battery housing and, in embodiments, the battery housing itself (or a portion thereof) may be used as the electrode. In this type of configuration, a feedthrough assembly having a feedthrough for each terminal of the battery may be used to facilitate electrically connecting the battery to the operational circuitry of the device. Typically, each feedthrough is configured to electrically isolate the respective energy supply from the battery housing (and, thus, from the sensing electrode that is electrically coupled to the battery housing).

SUMMARY

Embodiments of the disclosure include an implantable medical device (IMD) in which a negative battery terminal is electrically coupled to the case of the IMD such that the energy supply current pathway includes a portion of the case that is also shared by a sensing pathway associated with an electrode that is electrically coupled to the battery housing. According to some embodiments, the IMD may include a second feedthrough defined through the feedthrough assembly and a switch that enables the energy current pathway to be selectively coupled to, and isolated from, the IMD case.

In an Example 1, a medical device comprising: a case; a core assembly, the core assembly comprising operational circuitry enclosed within a core assembly housing, wherein the case comprises the core assembly housing; a battery assembly, the battery assembly comprising a battery enclosed within a battery housing, wherein the case further comprises the battery housing; and a feedthrough assembly disposed between the battery assembly and the core assembly, the feedthrough assembly comprising only one feedthrough, the feedthrough configured to facilitate connection of a battery terminal with the operational circuitry.

In an Example 2, the medical device of Example 1, the battery having a positive terminal and a negative terminal, the medical device further comprising: a first electrode coupled to, and electrically isolated from, the battery housing; and a second electrode electrically coupled to the case, wherein the second electrode is electrically coupled to the operational circuitry via a sensing pathway that includes a portion of the case, and wherein the battery is electrically coupled to the operational circuitry via an energy supply pathway that includes the portion of the case.

In an Example 3, the medical device of Example 2, wherein the positive terminal of the battery is electrically coupled to the operational circuitry via a feedthrough defined within a feedthrough assembly.

In an Example 4, the medical device of Example 3, wherein the energy supply pathway comprises an electrical connection between the negative terminal of the battery and the operational circuitry.

In an Example 5, the medical device of Example 4, wherein the portion of the case comprises at least one of a portion of the battery housing and a portion of the feedthrough assembly.

In an Example 6, the medical device of Example 5, the portion of the case comprising the portion of the feedthrough assembly, the feedthrough assembly comprising: a body having a lower engagement surface configured to at least partially engage an upper edge of the battery housing; and a pin coupled to an upper surface of the body, the pin configured to be coupled to a negative energy supply rail, wherein a portion of the energy supply pathway is defined between the lower engagement surface and the pin.

In an Example 7, the medical device of Example 6, the negative terminal of the battery comprising at least one conductive element coupled, at a first end, to an anode portion of the battery and coupled, at a second end, to the lower engagement surface.

In an Example 8, the medical device of Example 7, wherein the second end of the at least one conductive element is welded between the lower engagement surface of the body of the feedthrough assembly and the upper edge of the battery housing.

In an Example 9, a medical device comprising: a case; a core assembly, the core assembly comprising operational circuitry enclosed within a core assembly housing, wherein the case comprises the core assembly housing; a battery assembly, the battery assembly comprising a battery enclosed within a battery housing, wherein the case further comprises the battery housing; a first electrode coupled to, and electrically isolated from, the case; and a second electrode electrically coupled to the case, wherein the second electrode is electrically coupled to the operational circuitry via a sensing pathway that includes a portion of the case, and wherein the battery is electrically coupled to the operational circuitry via an energy supply pathway, wherein, in a first configuration, the energy supply pathway includes the portion of the case, and wherein, in a second configuration, the energy supply pathway is decoupled from the sensing pathway.

In an Example 10, the medical device of Example 9, further comprising a switch having a first position and a second position, wherein, when the switch is in the first position, the energy supply pathway is in the first configuration, and when the switch is in the second position, the energy supply pathway is in the second configuration.

In an Example 11, the medical device of Example 10, the battery having a positive terminal and a negative terminal, wherein the positive terminal of the battery is electrically coupled to the operational circuitry via a first feedthrough defined within a feedthrough assembly, wherein the energy supply pathway comprises an electrical connection between the negative terminal of the battery and the operational circuitry.

In an Example 12, the medical device of Example 11, wherein, in the second configuration, the negative terminal of the battery is electrically coupled to the operational circuitry via a second feedthrough defined within the feedthrough assembly.

In an Example 13, a method of manufacturing a medical device, comprising: providing a core circuitry assembly, the core circuitry assembly comprising operational circuitry; providing a battery assembly, the battery assembly comprising a battery enclosed within a battery housing, the battery comprising a first battery terminal and a second battery terminal; coupling a feedthrough assembly to the battery assembly, the feedthrough assembly comprising a body having a feedthrough defined therein; attaching a conductive pin to an upper surface of the feedthrough body; coupling the first battery terminal to the feedthrough; coupling the second battery terminal to at least one of the battery housing and the feedthrough body; coupling the conductive pin to the operational circuitry to form an energy supply pathway; electrically coupling a first electrode to the operational circuitry; electrically coupling a second electrode to the operational circuitry via a sensing pathway, wherein a portion of the sensing pathway includes a portion of the energy supply pathway; and enclosing the operational circuitry within a core assembly housing.

In an Example 14, the method of Example 13, the feedthrough assembly comprising a body having a lower engagement surface configured to at least partially engage an upper edge of the battery housing, wherein the portion of the energy supply pathway is defined between the lower engagement surface and the pin.

In an Example 15, the method of Example 14, wherein the first battery terminal comprises a positive battery terminal, and wherein the second battery terminal comprises a negative battery terminal, the negative battery terminal comprising at least one conductive element coupled, at a first end, to an anode portion of the battery, the method further comprising: welding a second end of the at least one conductive element between the lower engagement surface of the body of the feedthrough assembly and the upper edge of the battery housing.

In an Example 16, a medical device comprising: a case; a core assembly, the core assembly comprising operational circuitry enclosed within a core assembly housing, wherein the case comprises the core assembly housing; a battery assembly, the battery assembly comprising a battery enclosed within a battery housing, wherein the case further comprises the battery housing; a first electrode coupled to, and electrically isolated from, the case; and a second electrode electrically coupled to the case, wherein the second electrode is electrically coupled to the operational circuitry via a sensing pathway that includes a portion of the case, and wherein the battery is electrically coupled to the operational circuitry via an energy supply pathway that includes the portion of the case.

In an Example 17, the medical device of Example 16, the battery having a positive terminal and a negative terminal.

In an Example 18, the medical device of Example 17, wherein the positive terminal of the battery is electrically coupled to the operational circuitry via a feedthrough defined within a feedthrough assembly.

In an Example 19, the medical device of Example 18, wherein the energy supply pathway comprises an electrical connection between the negative terminal of the battery and the operational circuitry.

In an Example 20, the medical device of Example 19, wherein the portion of the case comprises at least one of a portion of the battery housing and a portion of the feedthrough assembly.

In an Example 21, the medical device of Example 20, the portion of the case comprising the portion of the feedthrough assembly, the feedthrough assembly comprising: a body having a lower engagement surface configured to at least partially engage an upper edge of the battery housing; and a pin coupled to an upper surface of the body, the pin configured to be coupled to a negative energy supply rail, wherein a portion of the energy supply pathway is defined between the lower engagement surface and the pin.

In an Example 22, the medical device of Example 21, the negative terminal of the battery comprising at least one conductive element coupled, at a first end, to an anode portion of the battery and coupled, at a second end, to the lower engagement surface.

In an Example 23, the medical device of Example 22, wherein the second end of the at least one conductive element is welded between the lower engagement surface of the body of the feedthrough assembly and the upper edge of the battery housing.

In an Example 24, the medical device of Example 16, wherein the operational circuitry includes a sense input component having a fully differential input configured to filter a common mode power noise from an input signal.

In an Example 25, the medical device of Example 16, wherein the second electrode comprises at least a portion of the battery assembly.

In an Example 26, a medical device comprising: a case; a core assembly, the core assembly comprising operational circuitry enclosed within a core assembly housing, wherein the case comprises the core assembly housing; a battery assembly, the battery assembly comprising a battery enclosed within a battery housing, wherein the case further comprises the battery housing; a first electrode coupled to, and electrically isolated from, the case; and a second electrode electrically coupled to the case, wherein the second electrode is electrically coupled to the operational circuitry via a sensing pathway that includes a portion of the case, and wherein the battery is electrically coupled to the operational circuitry via an energy supply pathway, wherein, in a first configuration, the energy supply pathway includes the portion of the case, and wherein, in a second configuration, the energy supply pathway is decoupled from the sensing pathway.

In an Example 27, the medical device of Example 26, further comprising a switch having a first position and a second position, wherein, when the switch is in the first position, the energy supply pathway is in the first configuration, and when the switch is in the second position, the energy supply pathway is in the second configuration.

In an Example 28, the medical device of Example 27, the battery having a positive terminal and a negative terminal, wherein the positive terminal of the battery is electrically coupled to the operational circuitry via a first feedthrough defined within a feedthrough assembly, wherein the energy supply pathway comprises an electrical connection between the negative terminal of the battery and the operational circuitry.

In an Example 29, the medical device of Example 28, wherein, in the second configuration, the negative terminal of the battery is electrically coupled to the operational circuitry via a second feedthrough defined within the feedthrough assembly.

In an Example 30, the medical device of Example 28, wherein the portion of the case comprises at least one of a portion of the battery housing and a portion of the feedthrough assembly.

In an Example 31, the medical device of Example 26, wherein the second electrode comprises at least a portion of the battery housing.

In an Example 32, a method of manufacturing a medical device, comprising: providing a core circuitry assembly, the core circuitry assembly comprising operational circuitry; providing a battery assembly, the battery assembly comprising a battery enclosed within a battery housing, the battery comprising a positive battery terminal and a negative battery terminal; coupling a feedthrough assembly to the battery assembly, the feedthrough assembly comprising a body having a feedthrough defined therein; attaching a conductive pin to an upper surface of the feedthrough body; coupling the positive battery terminal to the feedthrough; coupling the negative battery terminal to at least one of the battery housing and the feedthrough body; coupling the conductive pin to the operational circuitry to form an energy supply pathway; electrically coupling a first electrode to the operational circuitry; electrically coupling a second electrode to the operational circuitry via a sensing pathway, wherein a portion of the sensing pathway includes a portion of the energy supply pathway; and enclosing the operational circuitry within a core assembly housing.

In an Example 33, the method of Example 32, the feedthrough assembly comprising a body having a lower engagement surface configured to at least partially engage an upper edge of the battery housing, wherein the portion of the energy supply pathway is defined between the lower engagement surface and the pin.

In an Example 34, the method of Example 33, the negative terminal of the battery comprising at least one conductive element coupled, at a first end, to an anode portion of the battery, the method further comprising: welding a second end of the at least one conductive element between the lower engagement surface of the body of the feedthrough assembly and the upper edge of the battery housing.

In an Example 35, the method of Example 33, wherein the operational circuitry includes a sense input component having a fully differential input configured to filter a common mode power noise from an input signal.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIGS. 4A and 4B are schematic diagrams depicting an illustrative path coupling assembly, in accordance with embodiments of the disclosure.

FIG. 5 is a flow diagram depicting an illustrative method of manufacturing an IMD, in accordance with embodiments of the disclosure.

Figure 1:
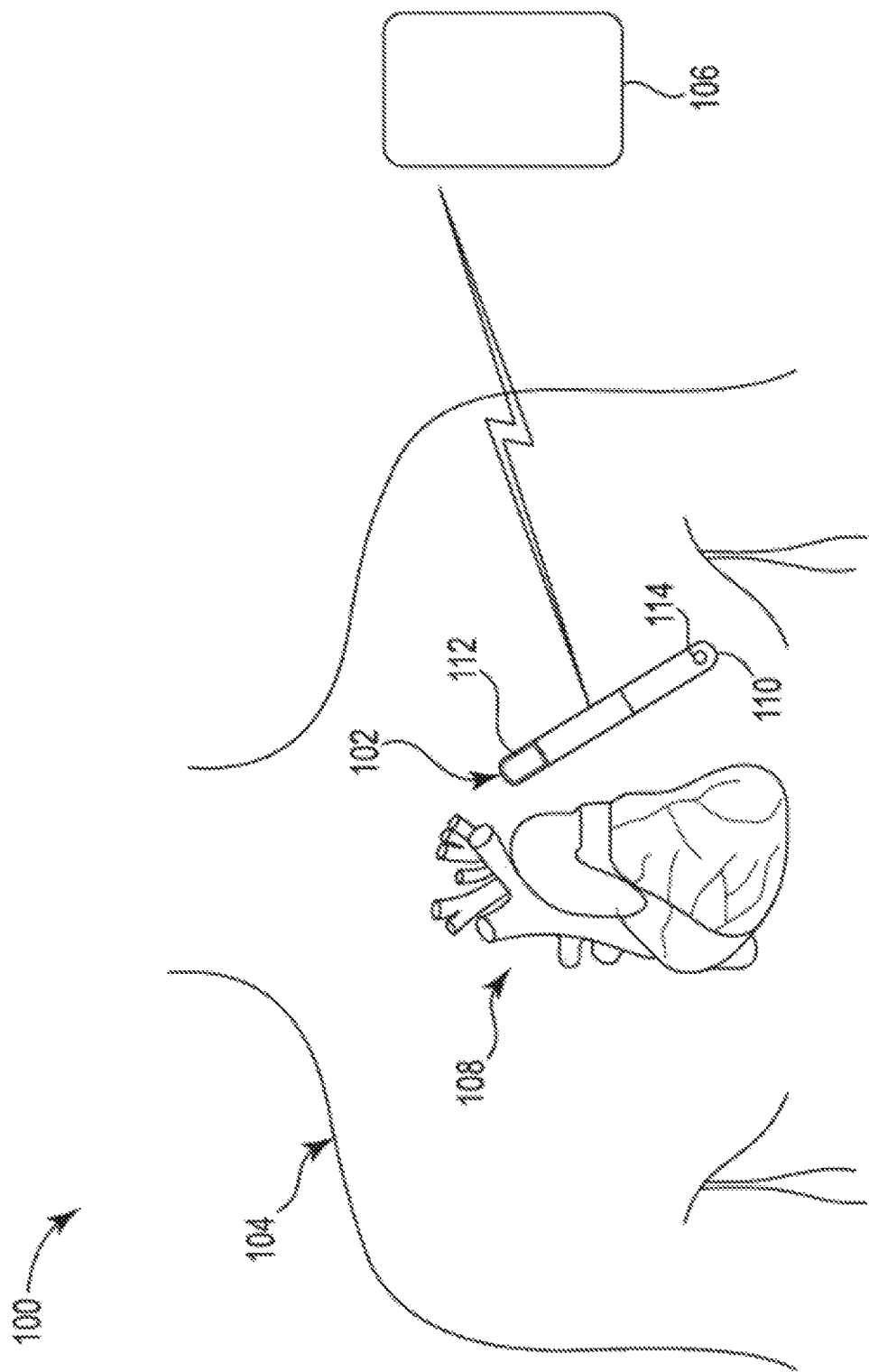
FIG. 1 is a schematic illustration depicting a patient monitoring system, in accordance with embodiments of the disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Embodiments of the disclosure include an implantable medical device (IMD) in which a battery terminal is electrically coupled to the case of the IMD such that the energy supply current pathway includes a portion of the case that is also shared by a sensing pathway associated with an electrode that is electrically coupled to the battery housing. In this manner, a feedthrough assembly disposed between the battery housing and a core assembly housing that encloses the operational circuitry of the IMD may be manufactured with only one feedthrough, thereby reducing the cost of manufacture. In embodiments, the portion of the case through which the energy supply current pathway and the sensing pathway are disposed may be configured to have a low resistance (e.g., micro-ohms or less) so that corruption of the sensing signal by the energy current is reduced to a tolerable level.

According to some embodiments, the IMD may include a second feedthrough defined through the feedthrough assembly and a switch that enables the energy current pathway to be selectively coupled to, and isolated from, the IMD case. In this manner, for example, the electrode can be selectively decoupled from the negative terminal, thereby enabling the IMD to drive signals through the electrode (e.g., for therapy).

FIG. 1 is a schematic illustration of a system 100 including an IMD 102 implanted within a patient's body 104 and configured to communicate with a receiving device 106. In embodiments, the IMD 102 may be configured to be implanted subcutaneously within an implantation location or pocket in the patient's chest or abdomen and may be configured to monitor (e.g., sense and/or record) physiological parameters associated with the patient's heart 108. The IMD 102 may be an implantable cardiac monitor (ICM) (e.g., an implantable diagnostic monitor (IDM), an implantable loop recorder (ILR), etc.) configured to record physiological parameters such as, for example, electrical signals (e.g., electrocardiograms), one or more cardiac activation signals, heart sounds, blood pressure measurements, oxygen saturations, and/or the like. The IMD 102 may be configured to monitor physiological parameters that may include one or more signals indicative of a patient's physical activity level and/or metabolic level, such as an acceleration signal. In embodiments, the IMD 102 may be configured to monitor physiological parameters associated with one or more other organs, systems, and/or the like. The IMD 102 may be configured to sense and/or record at regular intervals, continuously, and/or in response to a detected event. Such a detected event may be detected by one or more sensors of the IMD 102, another IMD (not shown), an external device (e.g., the receiving device 106), and/or the like. In addition, the IMD 102 may be configured to detect a variety of physiological signals that may be used in connection with various diagnostic, therapeutic, and/or monitoring implementations. For example, in embodiments, the IMD 102 may be configured to facilitate cardiac rhythm diagnostics, e.g., by monitoring heart rate, arrhythmias, and/or the like.

For example, the IMD 102 may include sensors or circuitry for detecting respiratory system signals, cardiac system signals, and/or signals related to patient activity. In embodiments, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

For purposes of illustration, and not of limitation, various embodiments of devices that may be used to record physiological parameters in accordance with the present disclosure are described herein in the context of IMDs that may be implanted under the skin in the chest region of a patient. In embodiments, however, the IMD 102 may include any type of IMD, any number of different components of an implantable system, and/or the like having a housing and being configured to be implanted in a patient's body 104. For example, the IMD 102 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the patient's body and/or the IMD 102. In various embodiments, the IMD 102 may include both defibrillation and pacing/CRT capabilities (e.g., a CRT-D device).

As shown, the IMD 102 may include a housing 110 having two electrodes 112 and 114 coupled thereto. According to embodiments, the IMD 102 may include any number of electrodes (and/or other types of sensors such as, e.g., thermometers, barometers, pressure sensors, optical sensors, motion sensors, and/or the like) in any number of various types of configurations, and the housing 110 may include any number of different shapes, sizes, and/or features. In embodiments, the IMD 102 may be configured to sense physiological parameters and record the physiological parameters. For example, the IMD 102 may be configured to activate (e.g., periodically, continuously, upon detection of an event, and/or the like), record a specified amount of data (e.g., physiological parameters) in a memory, and communicate that recorded data to a receiving device 106. In the case of an IDM, for example, the IMD 102 may activate, record cardiac signals for a certain period of time, deactivate, and activate to communicate the recorded signals to the receiving device 106.

In various embodiments, the receiving device 106 may be, for example, a programmer, controller, patient monitoring system, and/or the like. Although illustrated in FIG. 1 as an external device, the receiving device 106 may include an implantable device configured to communicate with the IMD 102 that may, for example, be a control device, another monitoring device, a pacemaker, an implantable defibrillator, a cardiac resynchronization therapy (CRT) device, and/or the like, and may be an implantable medical device known in the art or later developed, for providing therapy and/or diagnostic data about the patient and/or the IMD 102.

The system 100 may be used to implement coordinated patient measuring and/or monitoring, diagnosis, and/or therapy in accordance with embodiments of the disclosure. The system 100 may include, for example, one or more patient-internal medical devices, such as an IMD 102, and one or more patient-external medical devices, such as receiving device 106. In embodiments, the receiving device 106 may be configured to perform monitoring, and/or diagnosis and/or therapy functions external to the patient (i.e., not invasively implanted within the patient's body). The receiving device 106 may be positioned on the patient, near the patient, or in any location external to the patient.

In embodiments, the IMD 102 and the receiving device 106 may communicate through a wireless link. For example, the IMD 102 and the receiving device 106 may be coupled through a short-range radio link, such as Bluetooth, IEEE 802.11, and/or a proprietary wireless protocol. The communications link may facilitate uni-directional and/or bi-directional communication between the IMD 102 and the receiving device 106. Data and/or control signals may be transmitted between the IMD 102 and the receiving device 106 to coordinate the functions of the IMD 102 and/or the receiving device 106. In embodiments, patient data may be downloaded from one or more of the IMD 102 and the receiving device 106 periodically or on command. The physician and/or the patient may communicate with the IMD 102 and the receiving device 106, for example, to acquire patient data or to initiate, terminate, or modify recording and/or therapy.

The illustrative system 100 shown in FIG. 1 is not intended to suggest any limitation as to the scope of use or functionality of embodiments of the subject matter disclosed throughout this disclosure. Neither should the illustrative system 100 be interpreted as having any dependency or requirement related to any single component or combination of components illustrated in FIG. 1. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

Figure 2A:
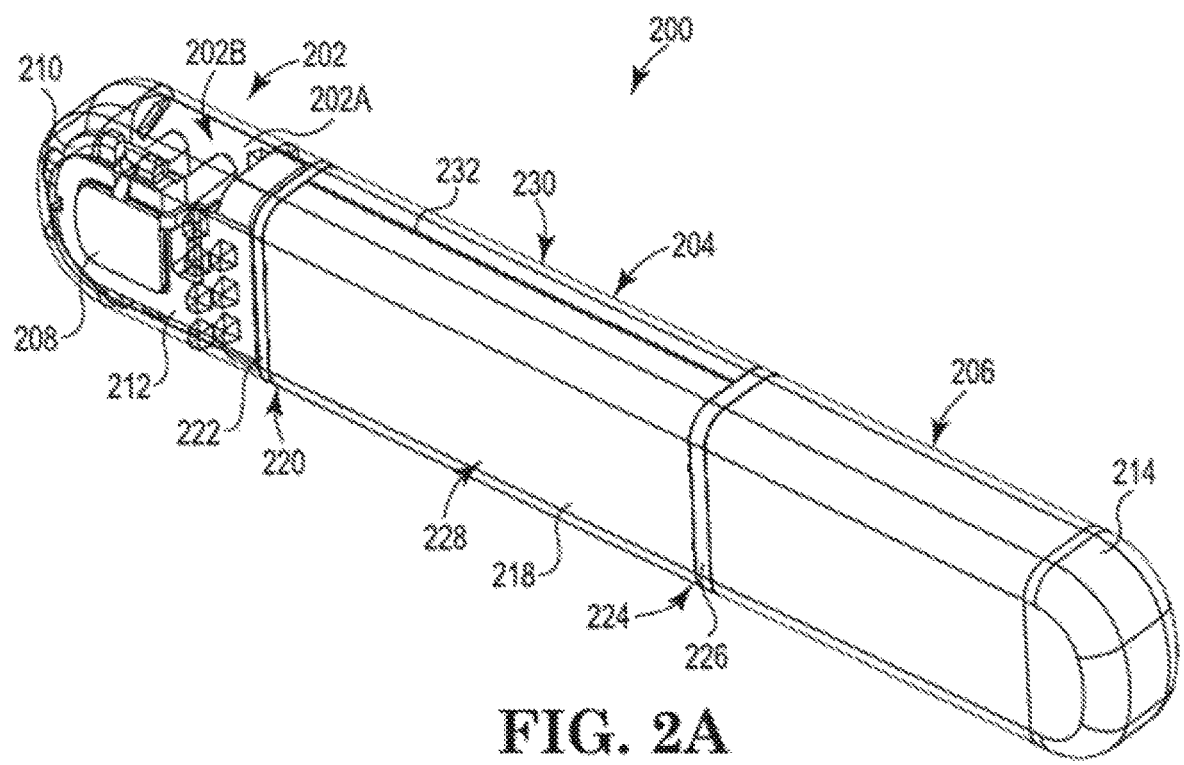
FIG. 2A is a perspective view of an implantable medical device (IMD), in accordance with embodiments of the disclosure.

FIG. 2A is a perspective view of an implantable medical device (IMD) 200, in accordance with embodiments of the disclosure. The IMD 200 may be, or may be similar to, the IMD 102 depicted in FIG. 1. As shown, the IMD 200 includes a hermetically sealed case 201, and may include a header 202 arranged at or near a first end 220 of a core assembly 204. A battery assembly 206 (which may include one or more batteries) is arranged near a second end 224 of the core assembly 204. The header 202 includes a housing 202A that encloses an interior region 202B. The header 202 may house various circuitry components within its interior, which may include a portion of the operational circuitry of the IMD 200. The housing 202A may contact a patient's bodily tissue when the IMD 200 is subcutaneously implanted in an implantation location or pocket in the patient's chest or abdomen. The interior region 202B of the header 202 may house circuit components (e.g., an electrode 208 and an antenna 210) positioned and supported by a scaffold assembly 212. As shown, the IMD 200 may include, in addition to the electrode 208, an electrode 214 electrically and/or physically coupled to the battery assembly 206. In embodiments, the electrode 214 may be integrated with the battery assembly 206, a housing of the battery assembly 206, and/or the like. In order to enable sensing of physiological parameters within the patient, the electrode 208 may be positioned to be flush with an interior surface of the housing 202A of the header 202. In other instances, the electrode 208 may be positioned by the scaffold assembly 212 to form a portion of an exterior surface of the housing 202A of the header 202.

Figure 2B:
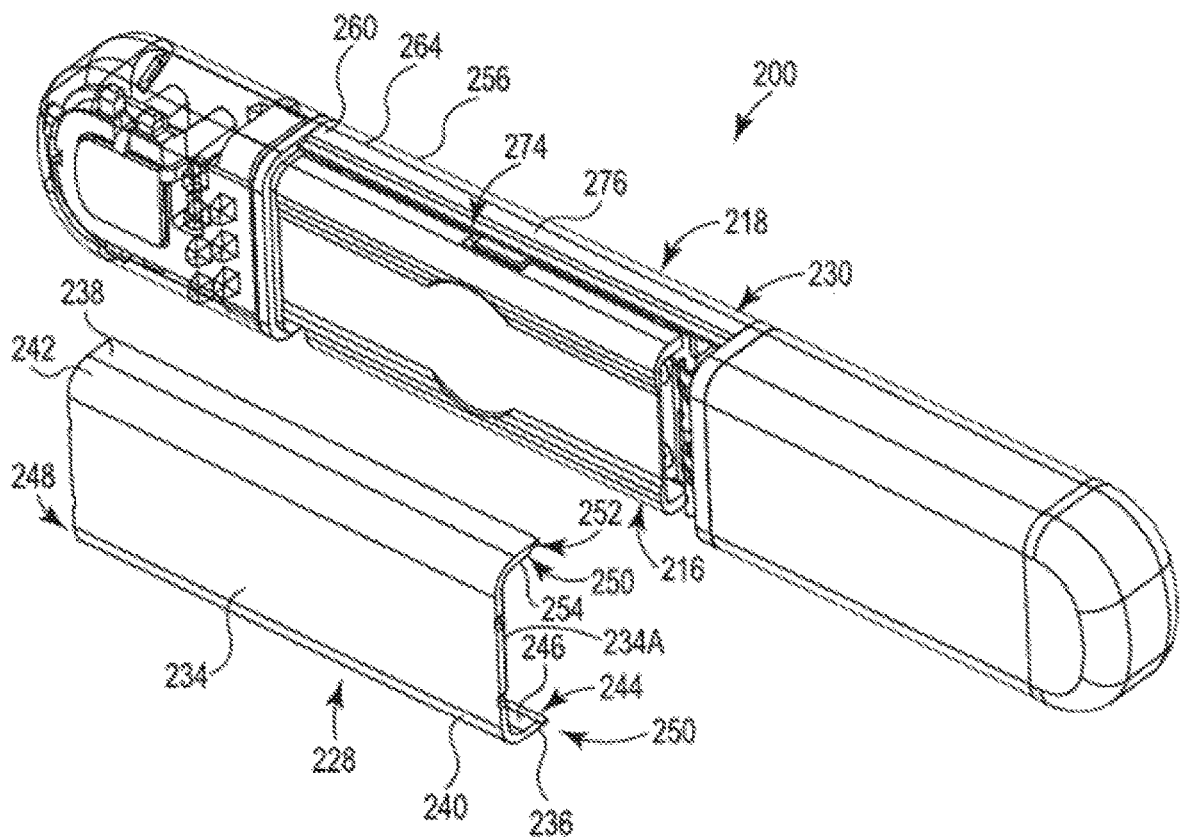
FIGS. 2B and 2C are partially-exploded perspective views of the IMD depicted in FIG. 2A, in accordance with embodiments of the disclosure.

As shown in FIG. 2B, the core assembly 204 includes a core circuitry assembly 216 enclosed within a core assembly housing 218. The core circuitry assembly 216 includes operational circuitry configured to perform one or more various functions described herein and may include processing circuitry, input circuitry, output circuitry, communication circuitry, and/or the like. Circuitry may include any number of different types of electrical and/or logical connections, components, and/or the like, and may include, for example, conductive elements (e.g., wires, conductive traces, etc.), processors (e.g., microprocessors, virtual processors, etc.), and/or other electrical and/or logical components. Thus, circuitry may include hardware, firmware, and/or software. The core assembly housing 218 is coupled, at the first end 220, to a first feed-through assembly 222, and coupled, at the second end 224, to a second feed-through assembly 226. The feed-through assembly 222 may be configured to provide a throughput for connections configured to connect the circuitry components of the header 202 (e.g., the electrode 208 and the antenna 210) to the core circuitry assembly 216. Similarly, the feed-through assembly 226 may be configured to provide a throughput for connections configured to connect one or more batteries (e.g., which are a part of the battery assembly 206) and/or the electrode 214 to the core circuitry assembly 216. In embodiments, the combination of the header housing, core assembly housing, battery housing, and feedthrough assembly surface form the case 201.

As illustrated in FIG. 2A, the core assembly housing 204 includes a first portion 228 configured to be coupled to a second portion 230 along a weld seam 232. The first portion 228 and second portion 230 may be coupled together by laser welding, seam welding, and/or the like. As shown, for example, in FIGS. 2B and 2C, the first portion 228 of the core assembly housing 218 includes a side wall 234, a lower wall 236, and an upper wall 238. The lower wall 236 and the upper wall 238 each extend, perpendicularly (or at least approximately perpendicularly) in a direction away from an inside surface 234A of the side wall 234. As shown, the lower wall 236 is coupled to the side wall 234 by a curved corner portion 240, and the upper wall 238 is coupled to the side wall 234 by a curved corner portion 242. In embodiments, the curved corner portions 240 and 242 may be integrated with the lower and upper walls 236 and 238, respectively, the side wall 234, and/or the like. That is, for example, the first portion 228 may be a single piece of metal, formed in a press or a mold. In embodiments, the curved corner portions 240 and 242 may be separate components. The curved corner portions 240 and 242 each may be designed to have any desirable radius of curvature. For example, the curved corner portions 240 and 242 each may be configured to have a radius of curvature that provides a desired amount of volume enclosed within the core assembly housing 218.

Figure 2C:
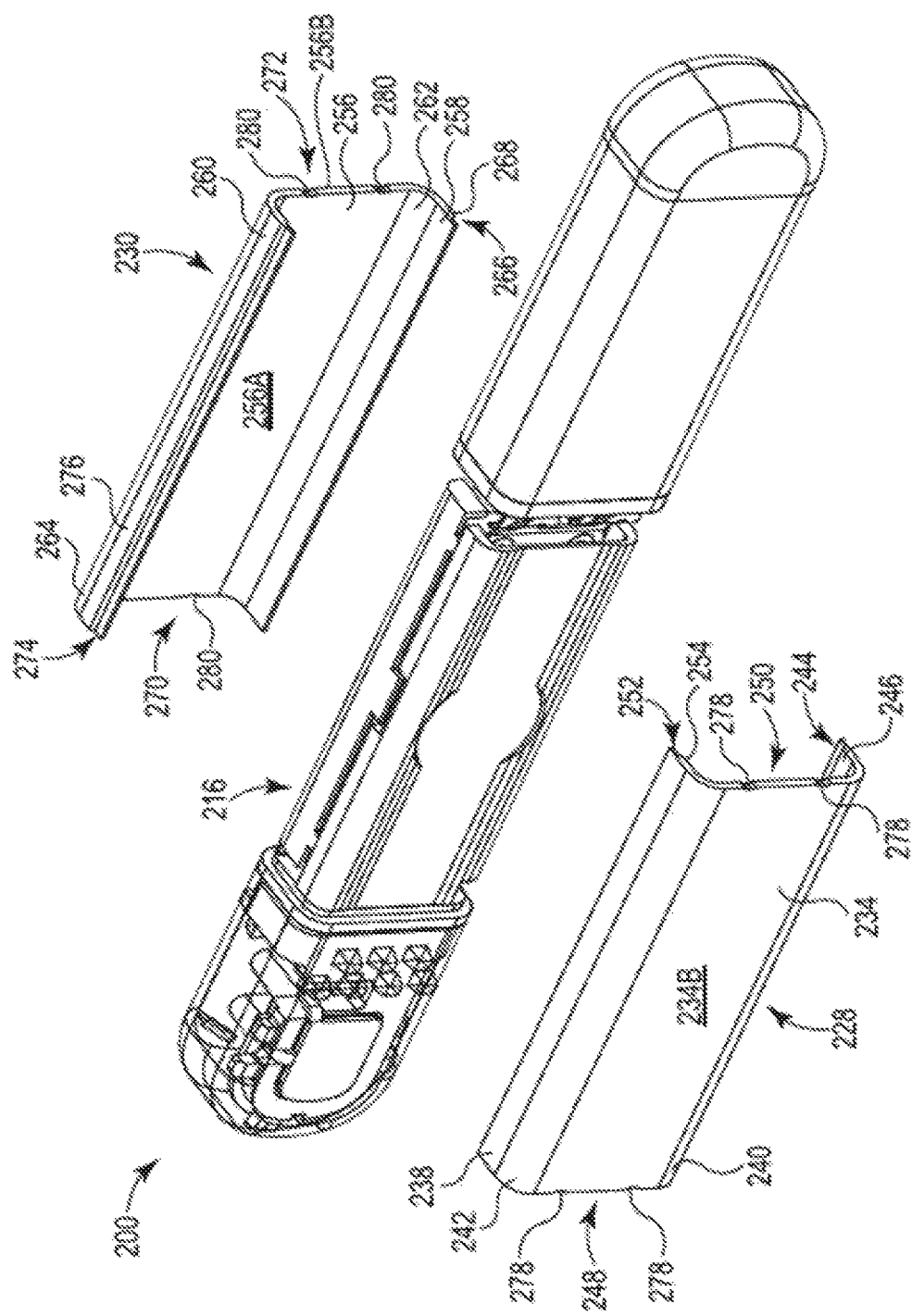

As illustrated, for example, in FIGS. 2B and 2C, the lower wall 236 includes a flange 244 that is recessed with respect to an inside surface 246 of the lower wall 236, and that extends from a first end 248 of the first portion 228 to a second end 250 thereof. The flange 244 may be a thinned portion of the lower wall 236. In embodiments, the flange 244 may be welded to the lower wall 236. Similarly, the upper wall 238 includes a flange 252 that is recessed with respect to an inside surface 254 of the upper wall 238, and that extends from the first end 248 of the first portion 228 to the second end 250 thereof. The flange 252 may be a thinned portion of the upper wall 238. In embodiments, the flange 252 may be welded to the upper wall 238.

As is also shown, for example, in FIGS. 2B and 2C, the second portion 230 of the core assembly housing 218 includes a side wall 256, a lower wall 258, and an upper wall 260. The lower wall 258 and the upper wall 260 each extend, perpendicularly (or at least approximately perpendicularly) in a direction away from an inside surface 256A of the side wall 256. As shown, the lower wall 258 is coupled to the side wall 256 by a curved corner portion 262, and the upper wall 260 is coupled to the side wall 256 by a curved corner portion 264. In embodiments, the curved corner portions 262 and 264 may be integrated with the lower and upper walls 258 and 260, respectively, the side wall 256, and/or the like. That is, for example, the second portion 230 may be a single piece of metal, formed in a press or a mold. In embodiments, the curved corner portions 262 and 264 may be separate components. The curved corner portions 262 and 264 each may be designed to have any desirable radius of curvature such as, for example, a radius of curvature that is identical or similar to the radius of curvature of each of the curved corner portions 240 and 242. For example, the curved corner portions 262 and 264 each may be configured to have a radius of curvature that provides a desired amount of volume enclosed within the core assembly housing 218.

As illustrated, for example, in FIGS. 2B and 2C, the lower wall 258 includes a flange 266 that is recessed with respect to an outside surface 268 of the lower wall 258, and that extends from a first end 270 of the second portion 230 to a second end 272 thereof. The flange 266 may be a thinned portion of the lower wall 258. In embodiments, the flange 266 may be welded to the lower wall 258. Similarly, the upper wall 260 includes a flange 274 that is recessed with respect to an outside surface 276 of the upper wall 260, and that extends from the first end 270 of the second portion 230 to the second end 272 thereof. The flange 274 may be a thinned portion of the upper wall 260. In embodiments, the flange 274 may be welded to the upper wall 260.

The core assembly housing 218 may also include notches 278 defined in the first and second ends 248 and 250, respectively, of the first portion 228, and extending from the inside surface 234A to the outside surface 234B of the side wall 234. Similarly, the core assembly housing 218 may also include notches 280 defined in the first and second ends 270 and 272, respectively, of the second portion 230, and extending from the inside surface 256A to the outside surface 256B of the side wall 256. The notches 278 and 280 may be an artifact of a progressive die manufacturing process in which the first and second portions 228 and 230 of the core assembly housing 218 are produced in a continuous strip and formed into shape in successive operations. The notches 278 and 280 may be left when the first and second portions 228 and 230 are broken away from the strip. In embodiments, the strip may be configured such that the notches are small enough to be consumed in the weld pool when the core assembly housing 218 is welded to the first and second feedthrough assemblies 222 and 226. For example, in embodiments, the notches 278 and 280 may extend into the portions 228 and 230 by less than or equal to approximately 0.003 inches.

The illustrative IMD 200 shown in FIGS. 2A-2C is not intended to suggest any limitation as to the scope of use or functionality of embodiments of the subject matter disclosed throughout this disclosure. Neither should the illustrative IMD 200 be interpreted as having any dependency or requirement related to any single component, feature, or combination of components or features illustrated in FIGS. 2A-2C. For example, in embodiments, the illustrative IMD 200 may include different and/or additional components and/or features. Any number of other components, features, or combinations of components or features can be integrated with the illustrative IMD 200 depicted in FIGS. 2A-2C, all of which are considered to be within the ambit of this disclosure. Additionally, any one or more of the components and/or features depicted in FIGS. 2A-2C can be, in embodiments, integrated with various ones of the other components and/or features depicted therein (and/or components and/or features not illustrated).

Moreover, as used herein, the terms "side wall," "lower wall," "upper wall," "upward," and "downward" are used to refer to the specific features to which they refer, but are characterized in the context of the illustrations for clarity and to describe relative orientations of features with respect to other features, and are not intended to imply any particular orientation of the IMD 200, or absolute (or preferred) orientations of features thereof. That is, for example, even if the IMD 200 were to be rotated around a longitudinal axis such that the outer surface 234B of the side wall 234 was parallel to a horizontal plane, the side wall 234 would still be referred to, for the purposes of this disclosure, as a "side wall."

Figure 3A:
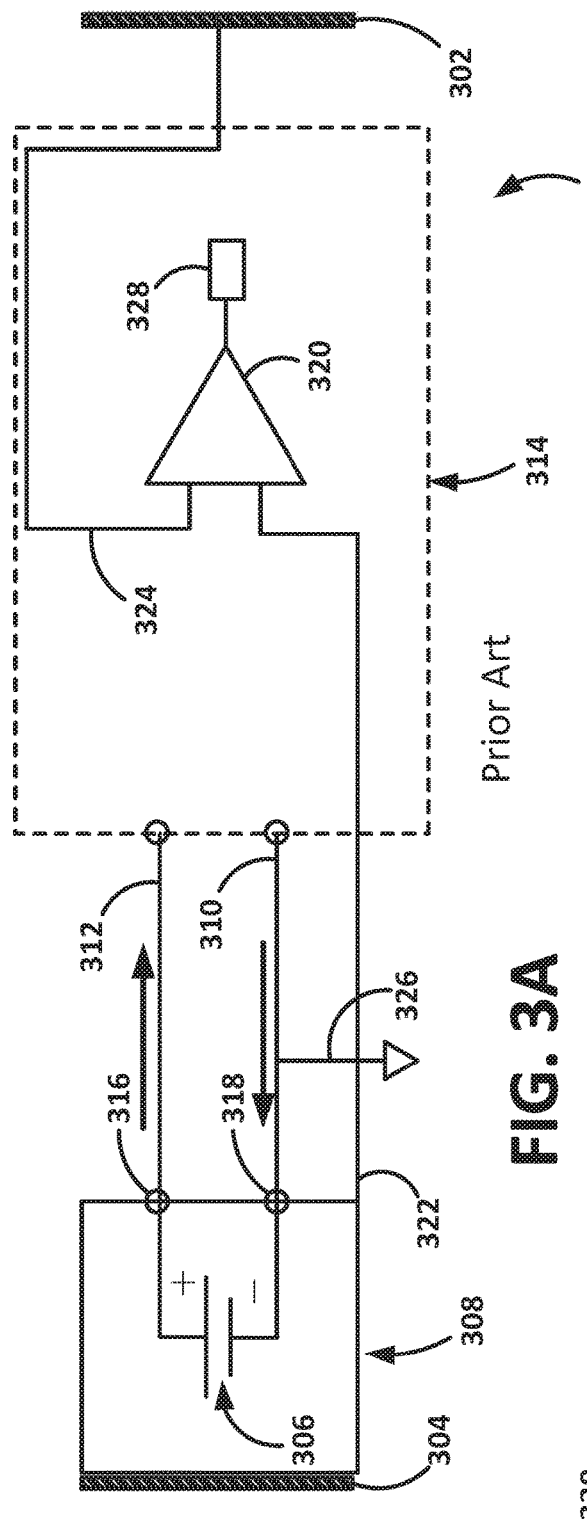
FIG. 3A depicts a conceptual circuit diagram depicting an illustrative circuit for an IMD, in accordance with the prior art.

FIG. 3A is a functional schematic diagram of circuitry 300 associated with an IMD in accordance with the prior art. The circuitry 300 depicted in FIG. 3A may be associated with the sensing of physiological signals by two electrodes 302 and 304. The circuitry 300 includes a battery 306 that is enclosed within a battery housing 308, to which the electrode 304 is electrically coupled. In embodiments, a portion of the battery housing 308 may function as the electrode 304. Supply rails 310 and 312 define the current path for delivery of energy to operational circuitry 314, and are electrically coupled to the battery 306 through feedthroughs 316 and 318, thereby electrically isolating the active components of the battery 306 from battery housing 308.

In operation, the electrodes 302 and 304 obtain a physiological signal from a patient, and transmit that obtained physiological signal to an input component 320 (e.g., a sense amplifier). As shown in FIG. 3A, the electrode 304 is directly coupled to a first input node of the input component 320 via a conductive element 322 (e.g., one or more conductive traces and/or wires), while the electrode 302 is directly coupled, via a conductive element 324 (e.g., one or more conductive traces and/or wires), to a second input node of the input component 320.

The conductive element 322 is directly coupled to the negative (or, in embodiments, positive) terminal of the battery 306, and to the common (ground) reference 326 of the operational circuitry 314. A different ground reference (not illustrated) may be utilized for another portion of components of the operational circuitry 314. The ground reference 326 may be used as a Kelvin Connection, joining the battery to the sensing electrode 304. In prior art IMDs, the coupling of the negative and/or positive terminal of the battery 306 to the conductive element 322 may be made at the intersection of the feedthrough 318 to effect a direct connection to the negative and/or positive supply rail 310, respectively. The configuration depicted in FIG. 3A may be designed to facilitate decoupling (e.g., electrically isolating) the energy supply current from the sense pathway. In some prior art implementations, the resistance of the conductive element 322 may be configured to be low as compared to the resistance of other pathways in the circuit to further decouple the sense pathway from the energy supply current pathway. As is further depicted in FIG. 3A, the output node of the input component 320 is coupled to processing circuitry 328. The processing circuitry 328 may include any number of different types of processing components, including, for example, one or more microprocessors, circuit components, and/or the like.

Figure 3B:
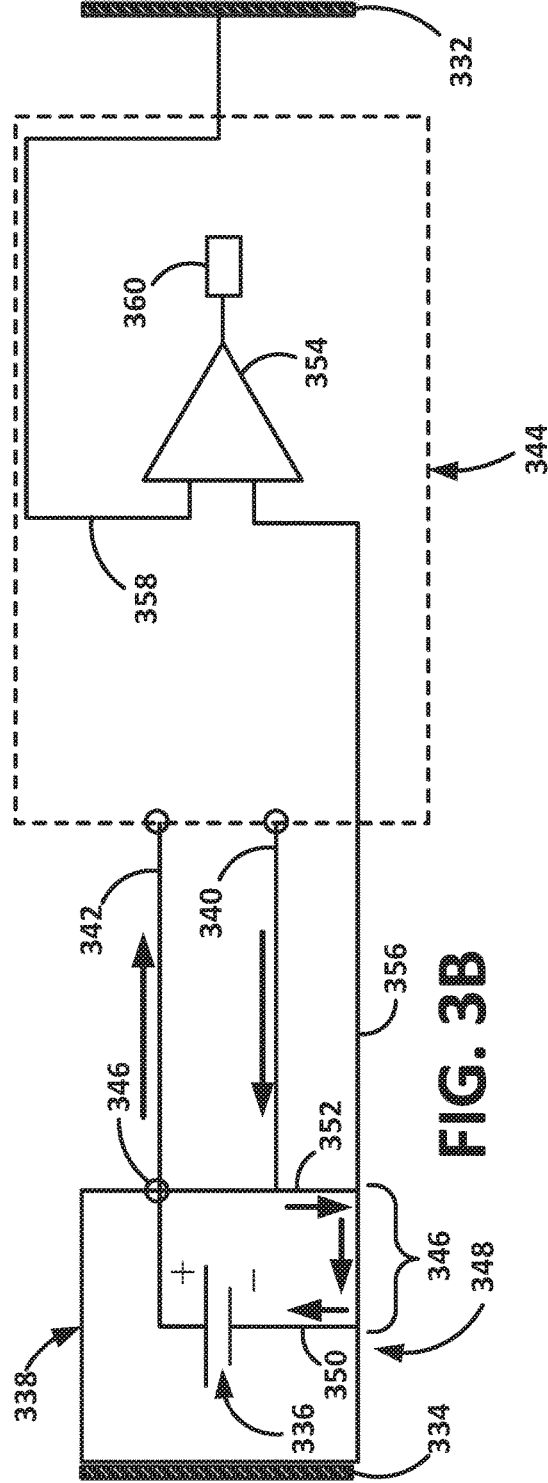
FIG. 3B depicts a conceptual circuit diagram depicting an illustrative circuit for an IMD, in accordance with the embodiments of the disclosure.

FIG. 3B is a functional schematic diagram of circuitry 330 associated with an IMD in accordance with the subject matter disclosed herein. The circuitry 330 depicted in FIG. 3B may be associated with the sensing of physiological signals by two electrodes 332 and 334. The circuitry 330 includes a battery 336 that is enclosed within a battery housing 338, to which the electrode 334 is electrically coupled. In embodiments, a portion of the battery housing 338 may function as the electrode 334. Supply rails 340 and 342 define the current path for delivery of energy to operational circuitry 344. The positive supply rail 342 is electrically coupled to the battery 336 through a feedthrough 346, and the negative supply rail 340 is electrically coupled to the battery 336 through a portion 346 of the battery housing 338 via a path coupling assembly 348. In embodiments, the negative supply rail 340 may be electrically coupled to the battery 336 through the feedthrough 346 and the positive supply rail 342 may be electrically coupled to the battery 336 through the portion 346 of the battery housing 338 via the path coupling assembly 348. Additionally, although the description refers to a particular positive/negative arrangement—e.g., an arrangement in which the negative battery terminal is electrically coupled to the negative supply rail via a portion of the housing—the description herein is intended to incorporate other arrangements. That is, for example, references to positive and/or negative terminals, supply rails, and/or the like, in the context of any one or more aspects of embodiments described herein may be reversed such that references to "positive" are references to "negative," and vice versa.

The path coupling assembly 348 may include, for example, a conductive element 350 electrically coupling the negative terminal of the battery 336 to the battery housing 338, and a conductive element 352 electrically coupling the battery housing 338 to the power supply rail 340. In embodiments, the conductive element 350 and/or the conductive element 352 may represent one or more conductive elements, a feedthrough assembly, one or more battery components, aspects of any of the foregoing, and/or the like. The energy supply current and the sensing path share a common pathway through the portion 346 of the battery housing 338. In this manner, the IMD may be manufactured with only one feedthrough from the battery housing 338 to the operational circuitry 344, thereby saving the manufacturing cost of creating a second feedthrough.

As can be seen from inspection of FIGS. 3A and 3B, the circuit configuration depicted in FIG. 3B may be similar to the circuit configuration depicted in FIG. 3A, with the exception of the configuration of the components that provide the negative supply rail connection to the battery. In operation, the electrodes 332 and 334 obtain a physiological signal from a patient, and transmit that obtained physiological signal to an input component 354 (e.g., a sense amplifier). As shown in FIG. 3B, the electrode 334 is directly coupled to a first input node of the input component 354 via a conductive element 356 (e.g., one or more conductive traces and/or wires), while the electrode 332 is directly coupled, via a conductive element 358 (e.g., one or more conductive traces and/or wires), to a second input node of the input component 354. As is further depicted in FIG. 3A, the output node of the input component 356 is coupled to processing circuitry 360.

The illustrative circuitry 330 shown in FIG. 3B is not intended to suggest any limitation as to the scope of use or functionality of embodiments of the subject matter disclosed throughout this disclosure. Neither should the illustrative circuitry 330 be interpreted as having any dependency or requirement related to any single component, feature, or combination of components or features illustrated in FIG. 3B. For example, in embodiments, the illustrative circuitry 330 may include different and/or additional components and/or features. Any number of other components, features, or combinations of components or features can be integrated with the illustrative circuitry 330 depicted in FIG. 3B, all of which are considered to be within the ambit of this disclosure. Additionally, any one or more of the components and/or features depicted in FIG. 3B can be, in embodiments, integrated with various ones of the other components and/or features depicted therein (and/or components and/or features not illustrated).

FIGS. 4A and 4B are schematic diagrams depicting an illustrative path coupling assembly in an IMD, in accordance with embodiments of the subject matter disclosed herein. The IMD may be, include, or be included in, the IMD 102 depicted in FIG. 1 and/or the IMD 200 depicted in FIGS. 2A-2C. Additionally, the IMD may include the circuitry 330 depicted in FIG. 3B, and the illustrative path coupling assembly may be, include, or be included in, the path coupling assembly 348 depicted in FIG. 3B.

As shown, the IMD includes a battery assembly 402 having a battery 404 enclosed within a battery housing 406. A feedthrough assembly 408 is disposed at a first end 410 of the battery housing 406. The feedthrough assembly 408 is made of a conductive material, and includes a feedthrough 412A configured to facilitate electrically coupling, via a conductive element 412B, the positive terminal of the battery 404 to operational circuitry (not shown) of the IMD. In embodiments, the positive terminal of the battery 404 may include one or more conductive elements 412B that are coupled to the cathode portions 414 of the battery 404. The negative terminal of the battery 404 includes one or more conductive elements that are coupled to the anode portions 416 of the battery 404.

In the illustrated embodiments, the negative conductive elements (which may, for example, be, include, or be included in, the conductive element 350 depicted in FIG. 3B) are depicted as being conductive ribbons 418, 420, and 422. Each conductive ribbon 418, 420, and 422 is coupled, at a first end (not shown), to an anode portion 416 of the battery 404 and extends toward the first end 410 of the battery housing 406. The second end of each conductive ribbon 418, 420, and 422 is disposed between an upper edge 424 of the battery housing 406 and a lower edge 426 of the feedthrough assembly 408. An anode pin 428 is coupled to the feedthrough assembly 408 and extends away from an upper end 430 of the feedthrough assembly 408. The anode pin 428 may be configured to be coupled to a negative supply rail (e.g., the negative supply rail 340 depicted in FIG. 3B) to facilitate electrically coupling the conductive ribbons 418, 420, and 422, via the pin 428, to the operational circuitry (not shown) of the IMD. In embodiments, for example, the anode pin 428 and/or the feedthrough assembly 408 (or aspects thereof) may be, include, or be included in the conductive element 352 depicted in FIG. 3B.

In this manner, an energy supply current path 430 has a common pathway through a portion 432 of the IMD housing 434 with the sensing path 436. In embodiments, the second ends of the conductive ribbons 418, 420, and 422 may form a portion of an external surface of the IMD, once the feedthrough assembly 408 has been welded to the battery assembly 402. The portion 432 of the IMD housing 434 may include, for example, a portion of the feedthrough assembly 408, a portion of a core circuitry assembly housing 438, and/or the like. According to embodiments, the negative terminal of the battery may be coupled to the IMD case in any number of other manners including, for example, via a pin welded to the inside of the case, connecting the terminal directly to the feedthrough assembly, and/or the like.

The illustrative path coupling assembly shown in FIGS. 4A and 4B is not intended to suggest any limitation as to the scope of use or functionality of embodiments of the subject matter disclosed throughout this disclosure. Neither should the illustrative path coupling assembly be interpreted as having any dependency or requirement related to any single component, feature, or combination of components or features illustrated in FIGS. 4A and 4B. For example, in embodiments, the illustrative path coupling assembly may include different and/or additional components and/or features. Any number of other components, features, or combinations of components or features can be integrated with the illustrative path coupling assembly depicted in FIGS. 4A and 4B, all of which are considered to be within the ambit of this disclosure. Additionally, any one or more of the components and/or features depicted in FIGS. 4A and/or 4B can be, in embodiments, integrated with various ones of the other components and/or features depicted therein (and/or components and/or features not illustrated).

FIG. 5 is a flow diagram depicting an illustrative method 500 of manufacturing an IMD, in accordance with embodiments of the disclosure. The IMD may be, for example, the IMD 102 depicted in FIG. 1, the IMD 200 depicted in FIGS. 2A-2C, and/or the like. Embodiments of the method 500 include providing a core circuitry assembly (block 502), which may include obtaining and/or assembling one or more portions of a core circuitry assembly such as, for example, by assembling an integrated circuit, coupling circuitry to a liner, and/or the like. The method 500 also may include providing a header (block 504), which may include obtaining and/or assembling one or more portions of a header such as, for example, by arranging circuit components (e.g., an electrode and an antenna) on a scaffold assembly and enclosing the scaffold assembly within a header assembly housing. The method 500 may also include providing a battery assembly (block 506) and providing feedthrough assemblies (block 508), which may include obtaining and/or assembling a battery assembly and/or a first and second feedthrough assembly.

As depicted in FIG. 5, embodiments of the method 500 also include coupling the feedthrough assemblies to the core circuitry assembly (block 510), and coupling the header to a first feedthrough assembly (block 512). Embodiments of the method 500 also include coupling the positive battery terminal to a feedthrough of a second feedthrough assembly and the negative battery terminal to the battery housing (block 514), attaching a conductive pin to the second feedthrough assembly (block 516), and coupling the battery assembly to the second feedthrough assembly (block 518).

In embodiments, the method 500 includes providing first and second portions of a core assembly housing (block 520). In embodiments, the core assembly housing portions may be molded, cut, and/or the like, and may be identical or similar to the core assembly housing portions 228 and 230 depicted in FIGS. 2A-2C. As shown in FIG. 5, embodiments of the method 500 also include welding the core assembly housing portions together to enclose the core circuitry assembly (block 522).

Figure 6:
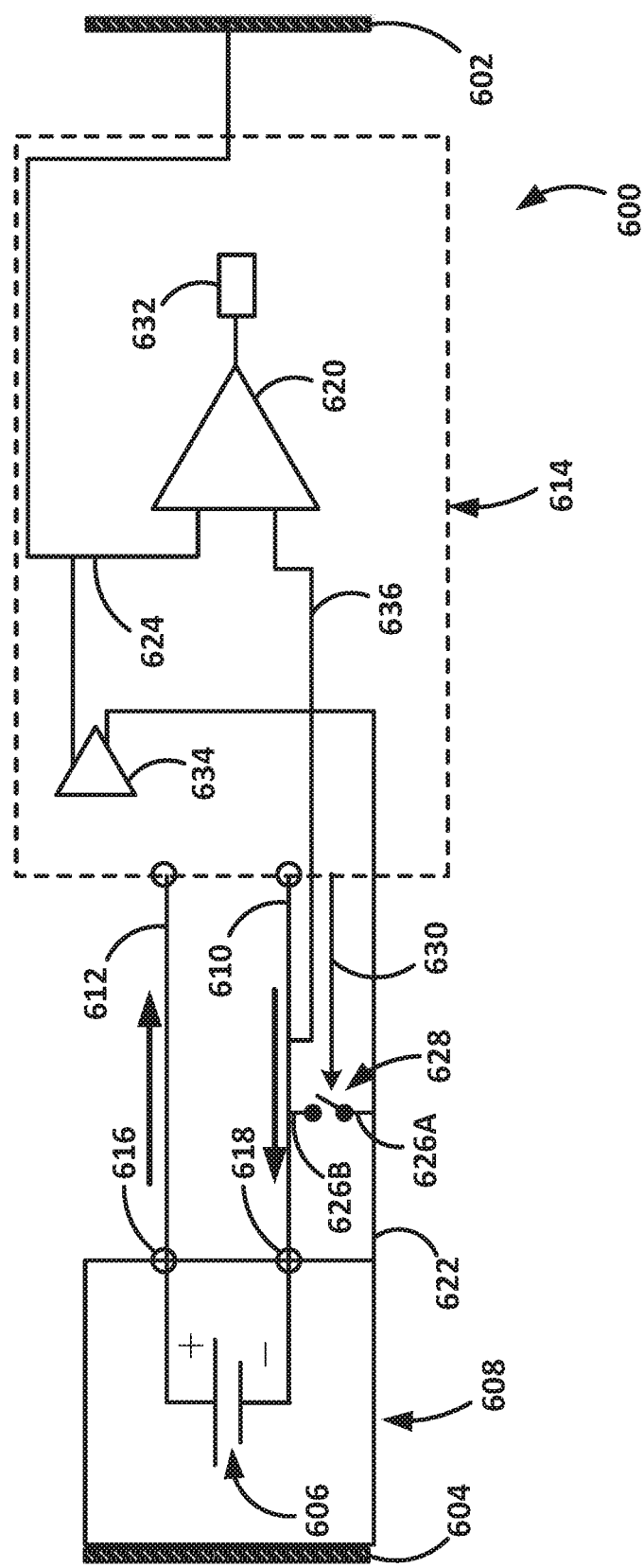
FIG. 6 depicts a conceptual circuit diagram depicting an illustrative circuit for an IMD, in accordance with embodiments of the disclosure.

According to embodiments, an IMD (e.g., the IMD 102 depicted in FIG. 1 and/or the IMD 200 depicted in FIGS. 2A-2C) may include a switched Kelvin connection, as shown, for example, in FIG. 6. FIG. 6 depicts a conceptual circuit diagram showing illustrative circuitry 600 having a switched Kelvin connection. Embodiments of the circuitry 600 depicted in FIG. 6 may be configured to facilitate optionally selecting a sensing mode, in which the IMD senses physiological electrical signals and a driving mode, in which a signal is driven onto the can (housing) of the IMD. In embodiments of the circuitry 600 depicted in FIG. 6, when the IMD is in a sense mode, the portion of circuit that is common for both a portion of the sense pathway and a portion of the powering pathway that are common is located on the circuit board, as opposed to in the can, as in other embodiments described herein.

The circuitry 600 depicted in FIG. 6 may be associated with the sensing of physiological signals by two electrodes 602 and 604. The circuitry 600 includes a battery 606 that is enclosed within a battery housing 608, to which the electrode 604 is electrically coupled. In embodiments, a portion of the battery housing 608 may function as the electrode 604. Supply rails 610 and 612 define the current path for delivery of energy to operational circuitry 614, and are at least selectively electrically coupled to the battery 606 through feedthroughs 616 and 618, thereby selectively electrically isolating the active components of the battery 606 from battery housing 608.

In operation, the electrodes 602 and 604 obtain a physiological signal from a patient, and transmit that obtained physiological signal to an input component 620 (e.g., a sense amplifier). As shown in FIG. 6, in a first configuration (e.g., a sense mode—an operational mode during which a switch 628 is closed), the electrode 604 is coupled (via a sense pathway) to a first input node of the input component 620. The supply rail 610 is coupled to a first input node of the input component 620, while the electrode 602 is directly coupled, via a conductive element 624 (e.g., one or more conductive traces and/or wires), to a second input node of the input component 620. In embodiments, the sense pathway includes the portion of a conductive element 622 (e.g., one or more conductive traces and/or wires) between the electrode 604 and the conductive element 626A, the switch 628, the conductive element 626B, the portion of the supply rail 610 between the intersection of the conductive element 626B and the supply rail 610 and the intersection of the conductive element 636 and the supply rail 610, and the conductive element 636. In the sense mode, then, the sense pathway and the powering pathway are common through the portion of the supply rail 610 between the intersection of the conductive element 626B and the supply rail 610 and the intersection of the conductive element 636 and the supply rail 610. The switch may be controlled via control signals 630 originating, e.g., from a controller, and/or another portion of the circuitry 600.

In a second configuration, (e.g., a driving mode), the switch 628 is open, in which case, the conductive element 622 (which may include, or be connected to, a portion of the IMD's housing—e.g., the electrode 604) is connected to a driver 634 via a conductive element 622, which enables the driver 634 to drive a signal onto the housing of the IMD. Additionally, as shown in FIG. 6, the driver 634 is connected, via the conductive element 624, to the electrode 602.

As is further depicted in FIG. 6, the output node of the input component 620 is coupled to processing circuitry 632. The processing circuitry 632 may include any number of different types of processing components, including, for example, one or more microprocessors, circuit components, and/or the like. According to embodiments, a switched Kelvin connection, such as that depicted in FIG. 6, may be useful for selectively configuring the IMD for different uses. That is, for example, in the first configuration, the IMD may be configured for performing sensing, while, in the second configuration, the IMD may be configured to deliver therapy (or otherwise provide some functionality that may involve driving a current through the electrode 604).

The illustrative circuitry 600 shown in FIG. 6 is not intended to suggest any limitation as to the scope of use or functionality of embodiments of the subject matter disclosed throughout this disclosure. Neither should the illustrative circuitry 600 be interpreted as having any dependency or requirement related to any single component, feature, or combination of components or features illustrated in FIG. 6. For example, in embodiments, the illustrative circuitry 600 may include different and/or additional components and/or features. Any number of other components, features, or combinations of components or features can be integrated with the illustrative circuitry 600 depicted in FIG. 6, all of which are considered to be within the ambit of this disclosure. Additionally, any one or more of the components and/or features depicted in FIG. 6 can be, in embodiments, integrated with various ones of the other components and/or features depicted therein (and/or components and/or features not illustrated).

Various modifications and additions can be made to the exemplary embodiments discussed without departing from the scope of the disclosed subject matter. For example, while the embodiments described above refer to particular features, the scope of this disclosure also includes embodiments having different combinations of features and embodiments that do not include all of the described features. That is, for example, embodiments may include one or more filters and/or other components that facilitate interpreting sensed physiological signals in the presence of some interference caused by having an energy supply current sharing a portion of the physical sense pathway. Accordingly, the scope of the disclosed subject matter is intended to embrace all such alternatives, modifications, and variations as fall within the scope of the claims, together with all equivalents thereof.

We claim:

1. A medical device comprising:
    a case;
    a core assembly comprising an operational circuitry enclosed within a core assembly housing, wherein the operational circuitry includes an input component comprising a first input node and a second input node, and the case comprises the core assembly housing;
    a battery assembly comprising a battery enclosed within a battery housing that includes a common pathway, wherein the case further comprises the battery housing, the battery having a positive terminal and a negative terminal, the battery assembly further comprising:
        a first conductive element having a first end electrically coupled to the positive terminal or to the negative terminal and a second end electrically coupled to a feedthrough assembly, and
        a second conductive element having a first end electrically coupled to the other of the negative terminal or the positive terminal and a second end mechanically and electrically coupled to an interior surface of the battery housing;
    a first electrode coupled to, and electrically isolated from, the case and coupled to the first input node; and
    a second electrode electrically coupled to the case, wherein the second electrode is electrically coupled to the second input node via a sensing pathway along the common pathway, and wherein the battery is electrically coupled to the operational circuitry via an energy supply pathway along the common pathway through which supply current is passed.

2. The medical device of claim 1, wherein the energy supply pathway comprises an electrical connection between the negative terminal of the battery and the operational circuitry.

3. The medical device of claim 1, the feedthrough assembly comprising:
    a body having a lower engagement surface configured to at least partially engage an upper edge of the battery housing; and
    a single anode pin coupled to an upper surface of the body, the anode pin configured to be coupled to a negative energy supply rail, wherein a portion of the energy supply pathway is defined between the lower engagement surface and the anode pin.

4. The medical device of claim 3, wherein the first conductive element is coupled, at the first end, to an anode portion of the battery and coupled, at the second end, to the lower engagement surface.

5. The medical device of claim 4, wherein the first conductive element, at the second end, is welded between the lower engagement surface of the body of the feedthrough assembly and the upper edge of the battery housing.

6. The medical device of claim 1, wherein the operational circuitry includes a sense input component having a fully differential input configured to filter a common mode power noise from an input signal.

7. The medical device of claim 1, wherein the second electrode comprises at least a portion of the battery assembly.

8. The medical device of claim 1, wherein the first conductive element and the second conductive element each comprises a conductive ribbon.

9. A medical device comprising:
    a case;
    a core assembly comprising an operational circuitry enclosed within a core assembly housing, wherein the operational circuitry includes an input component comprising a first input node and a second input node, and the case comprises the core assembly housing;
    a battery assembly comprising a battery enclosed within a battery housing, wherein the case further comprises the battery housing, the battery assembly further comprising:
        a first conductive element having a first end electrically coupled to a cathode portion or an anode portion of the battery and a second end electrically coupled to a feedthrough assembly, and
        a second conductive element having a first end electrically coupled to the other of the cathode portion or the anode portion and a second end mechanically and electrically coupled to an interior surface of the battery housing;
    a first electrode coupled to, and electrically isolated from, the case, wherein the first electrode is directly and electrically coupled to the first input node of the input component; and
    a second electrode electrically coupled to the case, wherein the second electrode is directly and electrically coupled to the second input node of the input component via a sensing pathway that includes a common pathway portion of the case, and wherein the battery is electrically coupled to the operational circuitry via an energy supply pathway,
    wherein, in a first configuration, the energy supply pathway includes the common pathway portion of the case, and wherein, in a second configuration, the energy supply pathway is decoupled from the sensing pathway.

10. The medical device of claim 9, further comprising a switch having an open position and a closed position, wherein, when the switch is in the open position, the energy supply pathway is in the first configuration, and when the switch is in the second position, the energy supply pathway is in the second configuration.

11. The medical device of claim 10, wherein the energy supply pathway comprises an electrical connection between a negative terminal of the battery and the operational circuitry.

12. The medical device of claim 11, wherein, in the second configuration, the negative terminal of the battery is electrically coupled to the operational circuitry via the feedthrough assembly.

13. The medical device of claim 9, wherein the second electrode comprises at least a portion of the battery housing.

14. The medical device of claim 9, wherein the first conductive element and the second conductive element each comprises a conductive ribbon.

15. A method of manufacturing a medical device, comprising:
   providing a core circuitry assembly comprising an ungrounded operational circuitry;
   providing a battery assembly comprising a battery enclosed within a battery housing, the battery comprising a positive battery terminal and a negative battery terminal;
   directly coupling a single feedthrough assembly to the battery assembly, the feedthrough assembly comprising a body, wherein no other feedthrough assemblies are directly coupled to the battery assembly;
   attaching a conductive pin to an upper surface of the body;
   coupling the negative battery terminal to the battery housing via one or more conductive elements;
   coupling the positive battery terminal to the feedthrough assembly via another conductive element;
   coupling the conductive pin to the operational circuitry to form an ungrounded energy supply pathway;
   electrically coupling a first electrode to the operational circuitry;
   electrically coupling a second electrode to the operational circuitry via an ungrounded sensing pathway, wherein a portion of the sensing pathway includes a portion of the energy supply pathway; and
   enclosing the operational circuitry within a core assembly housing.

16. The method of claim 15, wherein the body includes a lower engagement surface configured to at least partially engage an upper edge of the battery housing, wherein the portion of the energy supply pathway is defined between the lower engagement surface and the pin.

17. The method of claim 16, further comprising:
   welding an end of at least one of the multiple conductive elements between the lower engagement surface of the body and the upper edge.

18. The method of claim 16, wherein the operational circuitry includes a sense input component having a fully differential input configured to filter a common mode power noise from an input signal.

* * * * *